US008703476B2

(12) United States Patent
De Gier et al.

(10) Patent No.: US 8,703,476 B2
(45) Date of Patent: Apr. 22, 2014

(54) CARTRIDGE FOR AUTOMATED MEDICAL DIAGNOSTICS

(75) Inventors: Ronald Cornelis De Gier, Eindhoven (NL); Danny Genius Aldegonda Schaefer, Eindhoven (NL); Adrianus Wilhelmus Dionisius Maria Van Den Bijgaart, Eindhoven (NL); Chris Van Haag, Eindhoven (NL); Michiel De Jong, Eindhoven (NL)

(73) Assignee: Biocartis SA, Lausanne (CH)

( * ) Notice: Subject to any disclaimer, the term of this patent is extended or adjusted under 35 U.S.C. 154(b) by 1177 days.

(21) Appl. No.: 11/993,348

(22) PCT Filed: Jun. 26, 2006

(86) PCT No.: PCT/IB2006/052074
§ 371 (c)(1),
(2), (4) Date: Dec. 20, 2007

(87) PCT Pub. No.: WO2007/004103
PCT Pub. Date: Jan. 11, 2007

(65) Prior Publication Data

US 2010/0151565 A1 Jun. 17, 2010

(30) Foreign Application Priority Data

Jun. 30, 2005 (EP) .................................... 05105922

(51) Int. Cl.
*C12M 1/00* (2006.01)
*G01N 33/48* (2006.01)

(52) U.S. Cl.
USPC .................... 435/289.1; 435/287.2; 435/91.2; 435/287.3; 436/165; 422/68.1; 422/50

(58) Field of Classification Search
USPC ....................... 435/287.2, 289.1, 91.2, 287.3; 422/68.1, 50; 436/165
See application file for complete search history.

(56) References Cited

U.S. PATENT DOCUMENTS

| | | | |
|---|---|---|---|
| 666,359 A | 1/1901 | Schroeder | |
| D37,164 S | 10/1904 | Hilbom | |

(Continued)

FOREIGN PATENT DOCUMENTS

| | | | |
|---|---|---|---|
| JP | 10-26625 | 1/1998 | |
| JP | 2001-194373 | 7/2001 | ............... B01J 19/00 |

(Continued)

OTHER PUBLICATIONS

Japan Office action conducted in counterpart Japanese Appln. No. 2008-519048 dated Nov. 4, 2011 (Enlish transltion).

(Continued)

*Primary Examiner* — William H Beisner
*Assistant Examiner* — Danielle Henkel
(74) *Attorney, Agent, or Firm* — Kusner & Jaffe

(57) ABSTRACT

The present invention relates to a cartridge for the detection of the presence, absence and/or amount of a target nucleotide sequence in a sample comprising one or more nucleic acid sequences. The cartridge comprises a first component and a second component being connectable to each other, the first component comprising at least a first fluid opening and a first sealing surface and the second component comprising at least a second fluid opening and a second sealing surface. Upon connection of the first and second component the first and second fluid opening are placeable in fluid communication and the first and second sealing surfaces are placeable against each other to seal the fluid communication between the first and second fluid opening. The invention is characterized in that the cartridge comprises biasing means for biasing the second sealing surface in the direction of the first sealing surface.

18 Claims, 7 Drawing Sheets

(56) References Cited

U.S. PATENT DOCUMENTS

| | | | | |
|---|---|---|---|---|
| 4,479,760 | A | 10/1984 | Bilstad et al. | |
| 4,865,584 | A | 9/1989 | Epstein et al. | |
| D351,913 | S | 10/1994 | Hieb et al. | |
| 5,882,903 | A * | 3/1999 | Andrevski et al. | 435/91.2 |
| 5,892,993 | A | 4/1999 | Moriya | 396/317 |
| 6,156,270 | A | 12/2000 | Buechler | |
| 6,168,948 | B1 | 1/2001 | Anderson et al. | |
| 6,382,923 | B1 | 5/2002 | Gray | |
| 6,416,293 | B1 | 7/2002 | Bouchard et al. | |
| 6,653,124 | B1 | 11/2003 | Freeman | |
| 6,821,771 | B2 | 11/2004 | Festoc | |
| 6,870,185 | B2 * | 3/2005 | Roach et al. | 257/48 |
| 7,473,397 | B2 * | 1/2009 | Griffin et al. | 422/504 |
| 2002/0081669 | A1 | 6/2002 | Festoc | |
| 2003/0008308 | A1 | 1/2003 | Enzelberger et al. | |
| 2003/0073089 | A1 | 4/2003 | Mauze et al. | 435/6 |
| 2004/0197233 | A1 | 10/2004 | Nagaoka et al. | |
| 2004/0235154 | A1 | 11/2004 | Oh et al. | |
| 2004/0238355 | A1 | 12/2004 | Kimizuka | |

FOREIGN PATENT DOCUMENTS

| | | | | |
|---|---|---|---|---|
| JP | 2004-504828 | | 2/2004 | |
| JP | 2004-212326 | | 7/2004 | B81B 1/00 |
| JP | 2004-226067 | | 8/2004 | C12M 1/00 |
| JP | 2004-309145 | | 11/2004 | |
| JP | 2005-512071 | | 4/2005 | B01J 19/00 |
| WO | 03049860 | A1 | 6/2003 | |
| WO | WO03/049860 | * | 6/2003 | B01L 3/00 |
| WO | WO 2006/123578 | | 11/2006 | G01N 35/08 |

OTHER PUBLICATIONS

Ausubel et al., "Short Protocols in Molecular Biology," Third Edition, A Compendium of Methods from Current Protocols in Molecular Biology, John Wiley & Sons, Inc., 1995.

* cited by examiner

CARTRIDGE FOR AUTOMATED MEDICAL DIAGNOSTICS

The invention pertains to a cartridge for the detection of the presence, absence or amount of specific DNA or RNA sequences. The invention also pertains to the use of a system, optionally incorporating a cartridge, for the detection of the presence, absence or amount of specific DNA or RNA sequences.

Since the discovery of DNA, the technology relating to the detection of the presence, absence or amount of specific DNA or RNA sequences in a sample has taken an enormous flight. Especially PCR, the Polymerase Chain Reaction has contributed enormously to the development of assays of all types for the detection of the presence or absence of DNA or RNA sequences. At present, it is possible to collect DNA containing samples from an organism and determine the presence, absence or amount therein of certain specific DNA sequences (target sequences). Technology is available to perform such analysis for multiple target sequences at the same time, so-called multiplex detection of target sequences to thereby increase throughput.

At present, this type of analysis is not yet performed on a routine basis, such as for instance the measurement of the blood-glucose content in the case of diabetes. Generally, well-equipped laboratories are necessary, and careful protocols have to be used in order to avoid cross-contamination and to ensure that the results obtained are reliable i.e. false-positive or false-negative readings of the tests are minimised. However, as still a lot of manual labour is involved of extensively trained and supervised personnel, there remains a need in the art to overcome the above disadvantages of the present methods of DNA or RNA analysis. Especially RNA analysis is known to be very difficult because contamination happens very easy due to the present of minute amounts of RNA in the atmosphere and on the hands of the skilled analysts. Furthermore, the present methods of analysis are not only laborious, they are also time-consuming. Typically, an efficient procedure for a conventional DNA or RNA analysis takes about 6 hours due to, inter alia, all the handling between the various systems for the taking of samples, the isolation of DNA or RNA from the sample, the subsequent assay for the analysis of the presence, absence or amount of the target sequence in the sample, the processing of any results obtained and the corresponding presentation of the results.

Cartridge-based systems for the detection of DNA have been disclosed before.

For example U.S. Pat. No. 5,882,903 discloses a system for the detection of DNA. The system comprises a first assembly having one or more reaction chambers and a second assembly comprising a number of fluid chambers. The fluid chambers each hold fluid which is used during the detection of the DNA. These fluids comprise washing fluids, lysis fluid, and an amplification solution containing an amplification buffer and appropriate primers. The reaction chambers are used to perform the different steps of the detection such as washing, lysis, and amplification.

The first assembly of the known cartridge is a disk shaped component, and the second assembly is a ring shaped component, which can be placed exteriorly of the disk shaped component. The disk shaped component comprises at its circumference an exterior cylindrical sealing surface which is placed against an interior cylindrical sealing surface of the ring shaped component. In the sealing surfaces fluid openings are provided to bring the fluid chambers in fluid communication with the reaction chambers so that the different fluids can be exchanged between them.

A disadvantage of the known cartridge is that the first and second assembly have to be produced very accurately in order to provide a proper sealing between the first and second sealing surfaces. It is hereby of importance that the first and second assembly have to be movable with respect to each other in order to make it possible that different fluid openings of the first assembly and the second assembly can be brought in fluid communication, but at the same time a proper sealing should be obtained when a fluid opening of the first assembly is brought in fluid communication with a fluid opening of the second assembly. Due to these accuracy requirements of the dimensions of the first and second assembly, the cartridge is susceptible to a non proper sealing and therewith contamination between the first and the second assembly.

The object of the present invention is to provide a cartridge which does not have the above-mentioned problem.

This object is achieved with a cartridge according the preamble of claim 1, characterized in that the cartridge comprises biasing means for biasing the second sealing surface in the direction of the first sealing surface. By biasing the second sealing surface in the direction of the first sealing surface it is possible to obtain a better fit between these sealing surfaces which results in a better sealing. The biasing means may for instance comprise springlike elements which may force at least a part of the second component in said direction.

The biasing means may be comprised into one of the first or second component, or both components, but the biasing means may also be provided as a separate part.

In an embodiment the second component comprises a flexible part which is at least flexible in a direction perpendicular to the second sealing surface. By providing a flexible part which is at least flexible in the direction perpendicular to the second sealing surface, the second sealing surface can more easily be placed against the first sealing surface. Thereby, it is in such embodiment not required that the whole second component is biased in the direction of the first sealing surface.

In an embodiment the second component comprises two or more flexible parts, each having a second fluid opening and an associated second sealing surface and each being at least flexible in a direction perpendicular to the respective second sealing surface. By providing a different flexible part for different fluid openings and associated sealing surfaces, it is easier to obtain a proper sealing between the first and second component, since for each combination of fluid openings the first and second sealing surface can be placed against each other independent of the other fluid openings and associated sealing surfaces of the first and second component.

In an embodiment each of said first and second components comprises two or more fluid openings and corresponding first and second sealing surfaces, each of the first and second sealing surfaces being substantially flat, the planes of each of the first and second sealing surfaces, respectively, being substantially parallel to each other. In such embodiment all sealing surfaces lie substantially parallel to each other so that moving or biasing the second component in a certain direction (in general in the direction of the first component) improves the sealing between all the first and second sealing surfaces.

In an embodiment the first component is a main part of the cartridge, and the second component is a PCR body comprising one or more thermocycling chambers. In a preferred embodiment it is possible to provide a number of different PCR bodies, of which one can be selected to be connected to the main part of the cartridge. The different PCR bodies may for instance comprise a different number of reaction chambers, different sizes of the reaction chambers and/or different sets of primers which are especially designed to be used to detect a specific number of bacteria or such.

When using such separate PCR body which is connected to the main part by a user, it must be easy to correctly place and lock the PCR body on the main part. In order to make sure that a proper sealing between the fluid openings of the PCR body and the main part is easily obtained, it is therefore advantageous to make use of the present invention, whereby the sealing surface of a fluid opening of the PCR body is biased to an associated sealing surface of the main part of the cartridge.

In an embodiment the biasing means comprises a locking device to lock the second component on the first component. By combining the biasing means with a locking device, it is upon connection of the first and second component possible in a single operation to both lock the second component on the first component, and to bias in the second sealing surface of the second component in the direction of the first sealing surface of first component. The locking device may comprise any suitable means to lock the first component and second component, such as for instance click-fit, snap-on and screw means.

In an embodiment the second component is after connection the second component is with respect to the first component between at least a first position wherein the first and second fluid openings are in fluid communication and a second position wherein the fluid communication is obstructed. In certain embodiments of the cartridge is it desirable that the fluid communication between for instance two process chambers temporarily can be closed. With the above-mentioned construction it is possible to use the transition of the first component to the second component to (temporarily) close the fluid communication between the two fluid openings. Thus, since there is no separate valve device required, less space is needed between two connected process chambers. This is in particular advantageous since there will be less excess fluid needed to pump fluid from one process chamber to the other process chamber.

In an embodiment is at least of the first and second components provided with a seal element comprising the first fluid opening and sealing surface or second fluid opening and sealing surface, respectively, the valve element being configured to provide in the first position a fluid communication between the first and second fluid opening, and in the second position the obstruction of the fluid communication, the valve element further being configured to seal the first and second fluid opening from the environment in both the first and second position.

The present invention provides for a cartridge that is suitable for the detection of the presence, absence or amount of DNA and/or RNA. The detection of the presence, absence or amount of DNA and/or RNA is indicative, for instance, for the presence, absence or amount of a gene, an allele of a gene, a genetic trait or disorder, a polymorphism, a single nucleotide polymorphism (SNP) or of the presence of exogenous DNA or RNA in an organism, i.e. the presence, absence or amount of pathogens or bacteria in organisms. Through the present invention, suitable remedies can be developed for the preparation of medicaments for the treatment of the so diagnosed ailment. For instance, the detection in a sample (say, blood) from an organism (say, a human) of a pathogen (say, a virus) may thus lead to the diagnosis and the corresponding treatment (say, an antibiotic).

The cartridge may be of an exchangeable type which can be positioned in a reusable apparatus. Such cartridge may be disposable, recyclable or reusable, possibly after cleaning. By providing an exchangeable cartridge all parts that may come into contact with the sample may after the detection process be taken out of the apparatus and the cartridge may be exchanged for another one or cleaned before a next use. In other embodiments the cartridge may be an integral part of the reusable apparatus which is cleaned after each use.

In certain embodiments the apparatus comprises a control unit for controlling the isolation means, amplification means and/or the detection means. The control unit makes a automatic control of the isolation of DNA, the amplification of DNA and the detection of the amplified DNA possible.

The cartridge comprises one or more chambers in which the sample is held during the detection process. Such chambers may comprise an introduction chamber for introducing a sample in the cartridge, a lysis chamber for lysis of the cells in the sample, a washing chamber for washing, one or more thermocycling chambers for the amplification of the DNA, and a detection chamber which makes detection possible. It is also possible to provide a single chamber for one or more of the functions described in relation to the chambers. In such embodiment two or more chambers of the introduction chamber, lysis chamber, washing chamber, the thermocycling chamber(s), and the detection chamber may be combined in one single chamber.

During the different steps of the detection process the sample will be in a respective chamber. For this purpose, the sample will be transferred from one chamber to another chamber between two process steps. To make such transfer possible, each chamber is at least connected with another chamber by a fluid channel. In at least one, but preferably each of these fluid channels a valve means may be provided, which valve means preferably normally closes the fluid channel, but opens the fluid channel upon actuation of the valve means therewith placing the respective two chambers in fluid communication. The valve means may be designed as a one-way valve.

In certain embodiments the valve means are actuated by a valve actuation device. This valve actuation device is preferably arranged in the reusable apparatus.

In certain embodiments pump means are provided to pump the sample or any other fluid used in the detection process such as lysis buffer, reagents, washing and separation buffers, pre-amplification buffers, from one chamber to another chamber. These pump means may be actuated by pump actuation means which are preferably arranged in the reusable apparatus.

In certain embodiments, the system comprises means for data collection and/or means for data processing. These means are intended for use in the analysis of the detected DNA and/or for the interpretation of the results. In particular, in certain embodiments the data processing means that are able to link the presence, absence or amount of the target nucleic acid (or combination thereof) to a particular diagnosis. Such a data processing means can for example be in the form of a computer in combination with a database.

In certain embodiments, the system can also comprise the means for the introduction of one or more samples. Such sample introduction means may comprise any suitable device, such as a holding or docking device for the introduction of a sample from a syringe or pipette or such and may for instance comprise a one-way inlet valve, a septum, filters, and an overflow.

In certain embodiments, the system can also comprise lysis device. In the lysis device, that can be under the control of a control unit, the sample is treated to provide any nucleic acids in the sample in a form that they can be isolated from the sample. This lysis step typically includes the lysis of the cells such that cell and/or nuclear membranes are ruptured to thereby free the nucleic acids contained therein. Use can be made of means of physical or mechanical manipulation for the lysis step, but also chemical means can be used for lysis of the cells in the sample, such as a lysis buffer. Means for mixing can be provided to mix the sample and the lysis buffer Methods for lysis of cells are well known in the art from textbooks etc. If necessary such methods can be adapted for use in the present system. Any waste that is produced by the lysis step can be discarded, for instance to a waste device.

In certain embodiments, the sample insertion device and the lysis device can be combined.

In certain embodiments, the system can also comprise an enrichment device, optionally under the control of a control unit. The enrichment device enables the isolation of DNA from the lysed sample. To this end the enrichment device may be equipped with means for the isolation of DNA, such as magnetic particles. In this embodiment, the DNA or RNA of the present invention is absorbed onto magnetic particles. The absorbed nucleic acid material can be subjected to one or more washing, draining and/or purifying steps to remove any unwanted material such as remains of biological material contained in the sample and other sample components that are not DNA and/or RNA. When the absorbed DNA or RNA is of a desired purity, it can be desorbed or eluted from the magnetic particles. The enrichment device can also be equipped with means for physical or mechanical manipulation of the fluids for mixing, separating and isolating the DNA or RNA.

In certain embodiments, the system can also comprise the reagents that are necessary for the enrichment step, i.e. the isolation of the DNA or RNA, such as buffers, washing fluids, water, filters, magnetic beads etc.

In certain embodiments, the system can also comprise a waste device to accommodate any waste produced from the enrichment step such as used buffers, washing fluids and the like.

In certain embodiments, the different waste devices of the system can be separate for each different purpose or volume. In certain embodiments, two or more of the waste devices described herein can be combined to accommodate all waste that is produced by the method of the present invention.

In certain embodiments, the system further comprises a pre-amplification device, optionally under the control of a control unit. The pre-amplification device can be used, for instance for increasing the total amount of DNA or RNA to be analysed. Subjecting DNA or RNA obtained from the isolation step to a pre-amplification step can increase the total amount of DNA. This is advantageously, especially in the case of multiplex analysis, where multiple tests are performed on the isolated DNA, for instance to detect the presence absence or amount of multiple pathogens in one sample at a time. Suitable technology is available in the art for increasing the amount of DNA and is generally known as Whole Genome Amplification.

In the pre-amplification device, the isolated and purified DNA or RNA can be pre-treated with, inter alia an pre-amplification buffer and in case of whole genome amplification, with enzymes and DNTPs. The pre-amplification device can be connected to a waste device for the disposal of materials.

In certain embodiments, the pre-amplification device can also be used for carrying out certain assays for the detection of specific nucleic acids. Examples thereof are OLA-PCR like technologies such as provided by Applera (SNPplex), Keygene (SNPWave) and MRC-Holland (MPLA).

In certain embodiments, the system comprises an amplification device. The amplification device can be under the control of a control unit. The isolated DNA, optionally pre-treated as described herein elsewhere, is subjected in the amplification device to an amplification treatment in the amplification device. The amplification treatment comprises bringing the isolated DNA in contact with a set of PCR primers that are specific for the target nucleic acid, PCR enzymes such as one or more polymerases and dNTPs.

In certain embodiments, the amplification device holds a plurality of chambers. The plurality of chambers enables the isolated or pre-amplified DNA or RNA to be divided in portions and distributed amongst the chambers. In each chamber, an amplification step can be performed using a different set of primers. In this manner, multiplex analysis is provided in that one sample can be analysed for the presence, absence or amount of different target nucleic acids. IN the case of multiplex analysis, the primer set for each target nucleic acid can be equipped with a detectably different label, i.e. with a different fluorescent spectrum.

In certain embodiments, the system can also comprise reagents for the amplification of the isolated DNA such as enzymes, DNTPs etc.

In certain embodiments, the system can also comprise a detection device. The detection device can be under the control of a control unit. The detection device is suitable for the detection of the amplified DNA or RNA and preferably for the detection of the labels that are incorporated in the amplification products.

The detection device may detect based on label, length, mobility, nucleotide sequence, mass or a combination thereof. In certain embodiments a detection device can detect based on optical, electrochemical, magnetic or mobility (gel-electrophoresis). In principle any suitable detection device known from prior art may be used.

In certain embodiments, the system also comprises a data collection device to collect data obtained from the detection device.

In certain embodiments, the system also comprises a data processing device to process the data.

In one aspect of the present invention, there is provided a method for the detection of the presence, absence and/or amount of a target nucleotide sequence in a sample comprising one or more nucleic acid sequences, wherein the method comprises the steps of

- providing a sample from an organism;
- performing steps for isolation of the nucleic acid sequences from the sample;
- performing steps for amplification of (part of) the nucleic acid sequences to thereby provide amplicons;
- detecting the presence, absence and/or amount of the amplicons corresponding to the target nucleotide sequence amongst the nucleic acid sequences in the sample.

In certain embodiments, the method is performed in a cartridge as defined in the present application.

In certain embodiments, the target nucleotide sequence can be selected from the group consisting of DNA, genomic DNA, RNA, mRNA, cDNA, transgenic DNA, ETC. In certain embodiments, the organism is a human, a non-human animal, a micro-organism or a plant.

In certain embodiments, the sample is tissue, bodily fluids such as sputum, semen, blood, urine, and/or faeces.

In certain embodiments, the target nucleotide sequence is an exogenous sequence.

In certain embodiments, the target nucleic sequence is a pathogen.

In certain embodiments, the sample comprising the nucleic acid sequences is subjected to lysis to free the contained nucleic acid sequences. In certain embodiments, the lysed sample is subjected to a sequence of washing and collecting steps as are themselves known in the art and described in standard text books that aim at the isolation of the nucleic acids from the sample. These steps can be performed in a single step or as a sequence of multiple steps. After isolation of the nucleic acids from the sample, the nucleic acids can be subjected to an amplification reaction using primers that are selective for the detection of the target nucleic acid.

Nucleic acid amplification methods usually employ two primers, dNTPs, and a (DNA) polymerase. A preferred method for amplification is PCR. "PCR" or "Polymerase Chain Reaction" is a rapid procedure for in vitro enzymatic amplification of a specific DNA segment. The DNA to be amplified is denatured by heating the sample. In the presence of DNA polymerase and excess deoxynucleotide triphosphates, oligonucleotides that hybridise specifically to the target sequence prime new DNA synthesis. One round of synthesis results in new strands of determinate length, which, like the parental strands, can hybridise to the primers upon denaturation and annealing. The second cycle of denaturation, annealing and synthesis produces two single-stranded products that together compose a discrete double-stranded product, exactly the length between the primer ends. This discrete product accumulates exponentially with each successive round of amplification. Over the course of about 20 to 30 cycles, many million-fold amplification of the discrete fragment can be achieved. PCR protocols are well known in the art, and are described in standard laboratory textbooks, e.g. Ausubel et al., Current Protocols in Molecular Biology, John Wiley & Sons, Inc. (1995). Other multiplex and/or isothermal amplification methods that may be applied include e.g. LCR, self-sustained sequence replication (3SR), Q-β-replicase mediated RNA amplification, rolling circle amplification (RCA) or strand displacement amplification (SDA).

Detection of the labelled amplicons is performed by a detector to result in detection data. The detector is of course dependent on the general system with which the discrimination between the amplicons of the target sequences is performed but is also depending on the label that is present on the primer, such as a fluorescent or a phosphorescent label. To discriminate between different target sequences in the sample preferably a difference in fluorescence spectrum of the respective corresponding amplicons is used. In certain embodiments, at least one of the primers comprises a label, preferably the forward primer comprises a label. The label can be selected from a large group, amongst others comprising fluorescent and/or phosphorescent moieties such as dyes, chromophores, or enzymes, antigens, heavy metals, magnetic probes, phosphorescent moieties, radioactive labels, chemiluminescent moieties or electrochemical detecting moieties. In certain embodiments the label is a fluorescent or phosphorescent dye. Examples of such dyes are FAM, HEX, TET, JOE, NED, and (ET-) ROX. Dyes such as FITC, Cyt, Texas Red, TAMRA, Alexa fluor 488™, BodipyFL, Rhodamine 123, R6G, Bodipy 530, Alexafluor™532.

By using different primer sets each containing a different label, the number of target sequences that can be discriminated in a sample and hence the number of target sequences in a sample that can be detected can be increased by using additional labels. The maximum number of labels that can be used in one sample in a multiplex method is governed mostly by the limitations in the detection capabilities of the available detection platforms.

In certain embodiments, the amplification is performed using the Polymerase Chain Reaction with at least one forward and at least one reverse primer that are selective for the target sequence and not for any other sequence in the sample.

In certain embodiments, at least one of either the forward or the reverse primer is labelled.

In certain embodiments, the amplification step is preceded or replaced by an assay for the detection of nucleic acids in samples.

In certain embodiments, the amplicons are detected based on label, length, mobility, nucleotide sequence, mass or a combination thereof.

In certain embodiments, the amplicons are detected based on optical, electrochemical, or magnetic detection.

Figure 5:
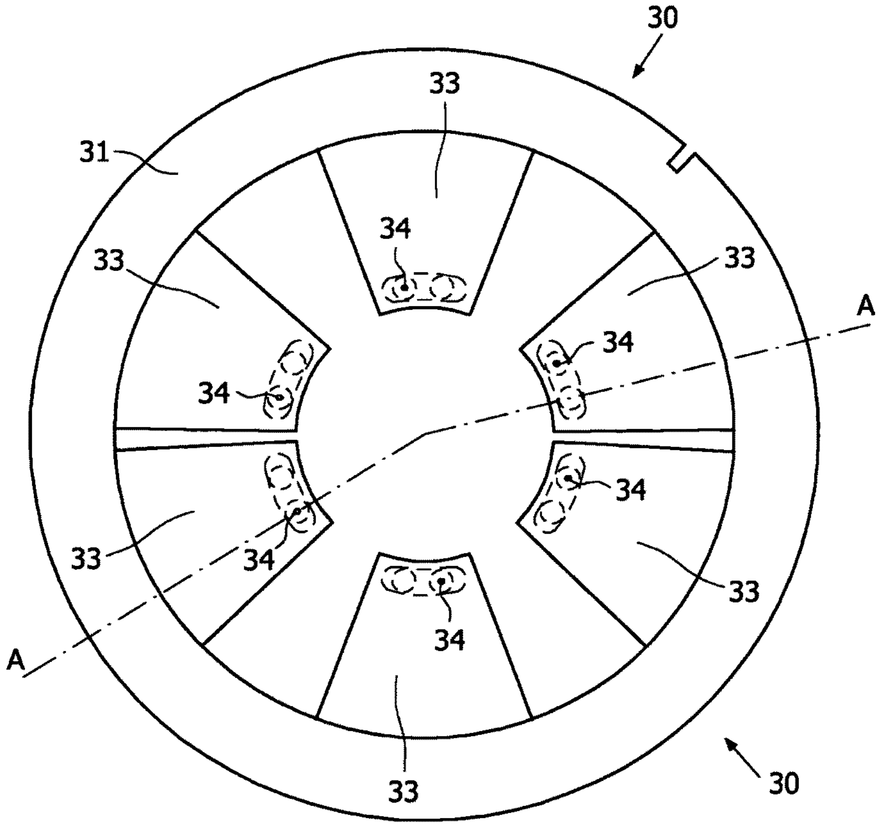
Figure 6:
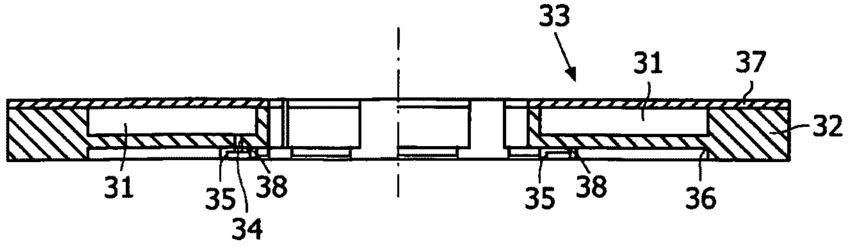
Figure 7:
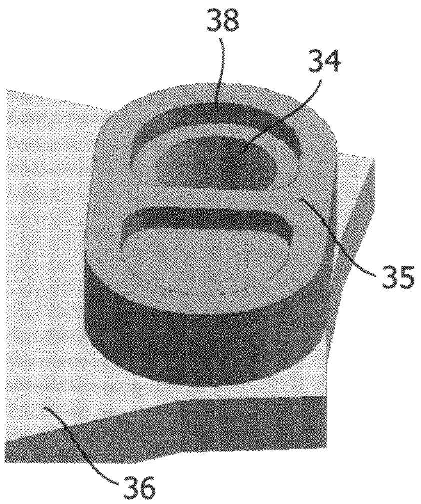
Figure 8:
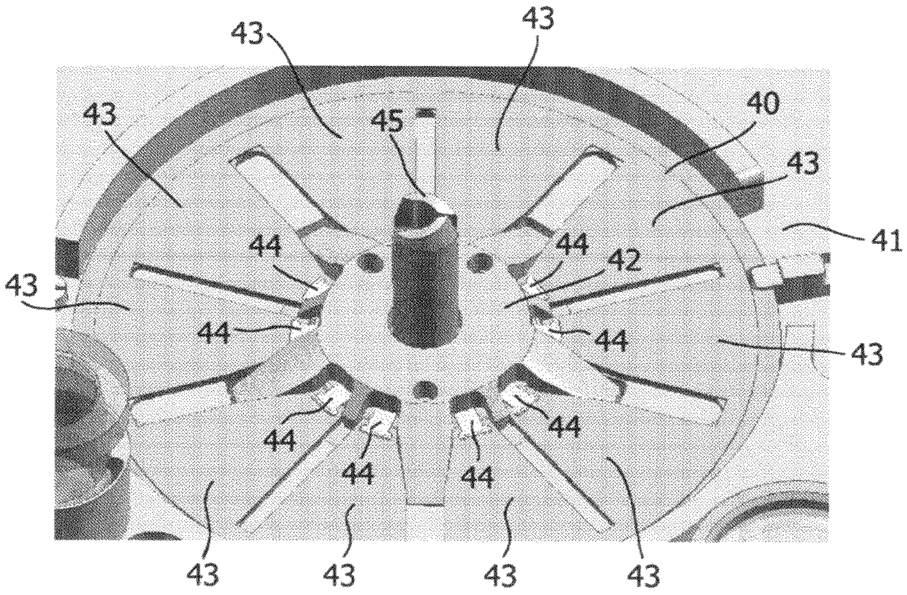

FIG. 5 shows a more detailed top view of a possible embodiment of a PCR disc according to the present invention, FIG. 6 shows a cross section of the PCR disc of FIG. 5, FIG. 7 shows a perspective detailed view of a seal element according to the invention; and FIG. 8 shows a perspective view of a PCR disk which is connected with a locking device to a main part of the cartridge, the locking device comprising biasing means.

Figure 1:
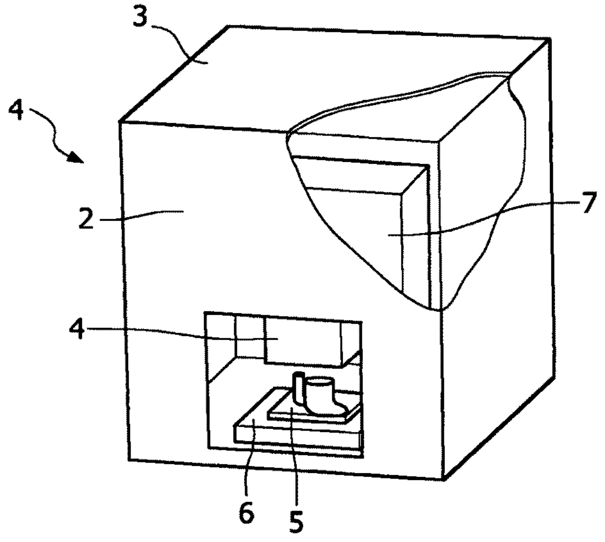
FIG. 1 shows a perspective view of a system according to an embodiment of the invention.

FIG. 1 shows an embodiment of a system for the detection of the presence, absence and/or amount of a target nucleotide sequence in a sample comprising one or more nucleic acid sequences, in general indicated with the reference numeral 1. The system comprises a reusable apparatus 2 with a housing 3 (partly broken away).

In the apparatus 2 a recess 4 is provided. An exchangeable cartridge 5 is removably positioned in this recess 4. The cartridge 5 may be reusable, recyclable or disposable.

In order to make detection possible the cartridge 5 comprises introduction means for the introduction of a sample, isolation means for the isolation of DNA, amplification means for the amplification of DNA, and detection means for the detection of amplified DNA. The introduction means, isolation means, amplification means and/or detection means may be arranged on the cartridge and/or in the reusable apparatus. In general it is preferred to arrange in the apparatus 2 all parts of the system 1 which normally do not come into contact with the sample. The sample is held throughout the detection process in cartridge which works as a cartridge.

Hereinafter a preferred embodiment of the arrangement of the introduction means, isolation means, amplification means and/or detection means is described. However, other embodiments are also possible.

The apparatus 2 comprises a control unit 7 for automatically controlling the different steps of the detection process as will be described hereinafter.

Further, the apparatus 2 comprises one or more actuation devices for the actuation of different elements arranged on the cartridge. These actuation devices may comprise one or more pump means actuation devices for the actuation of one or more pump means for pumping fluid, one or more valve actuation devices for actuation of one or more valves being arranged in a fluid channel in the cartridge, and other actuation devices such as mechanical actuation devices for providing, for example, a rotary or translating movement to one or more parts of the cartridge.

In the apparatus a detection device is provided which may detect the presence, absence and/or amount of DNA. For this purpose the DNA may be placed in a detection chamber which is arranged on the cartridge. The detection device may work on an optical, electrochemical, or magnetic principle as known from prior art. Any other suitable detection method may be applied.

The apparatus may further comprise a data collection device and a data processing device to collect data obtained from the detection device and to process these data, respectively.

The apparatus 2 comprises a carrier 6 for supporting the cartridge 5. The carrier 6 is movable in a vertical direction between a lower position (in which the carrier is shown) and a higher position. In the lower position the cartridge 5 can be placed on or taken from the carrier 6. The higher position is the working position in which the cartridge 5 is positioned during the detection process. In this higher position the cartridge is clamped between the carrier 6 and the a number of devices being arranged on the cartridge, such as pump means, valves, mechanical means, and a detection chamber may cooperate with corresponding devices being arranged in the apparatus 2, such as pump means, valve and other mechanical actuation devices, and a detection device.

In an alternative embodiment it is also possible that a part of the apparatus 2 comprising the corresponding devices can be moved towards and away from a cartridge placed in the apparatus 2.

Figures 1, 2:
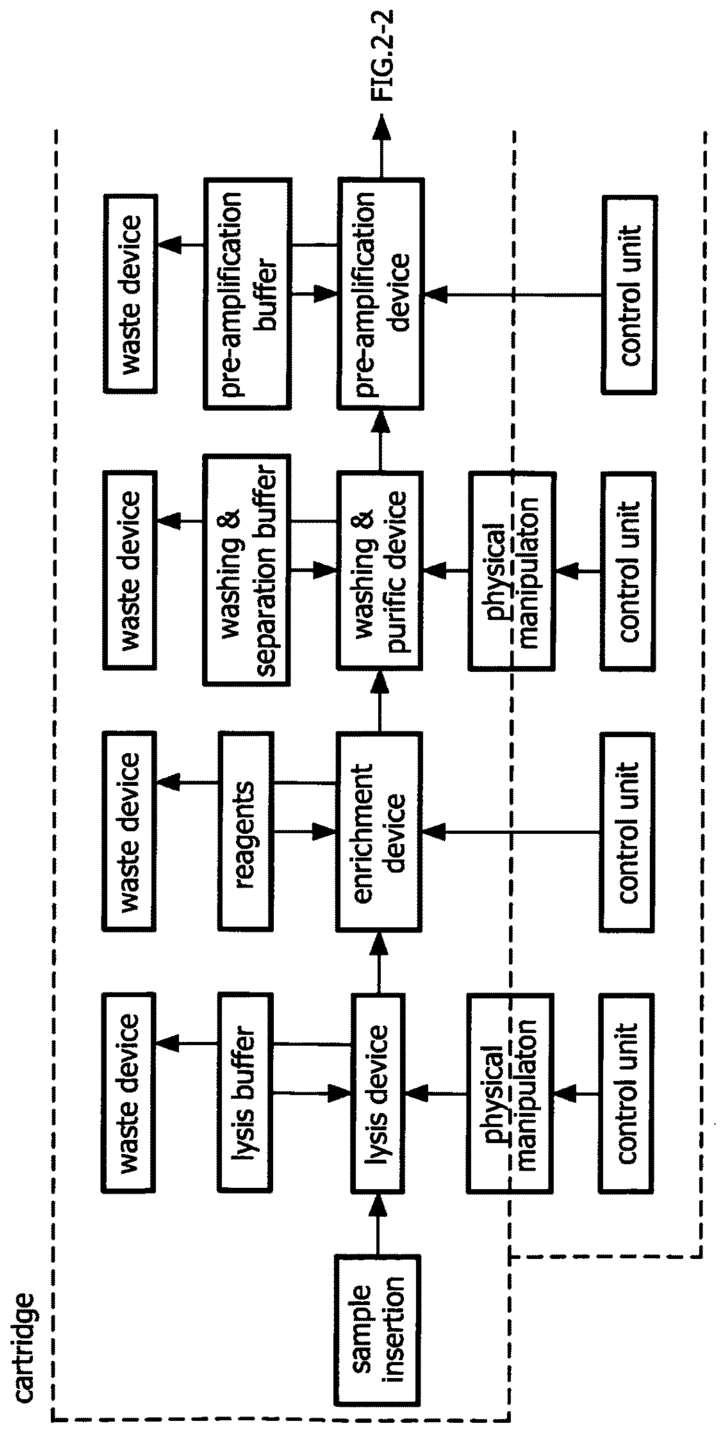
FIG. 2 shows a schematic block diagram of the architecture of an embodiment of the system according to the invention.
Figure 2:
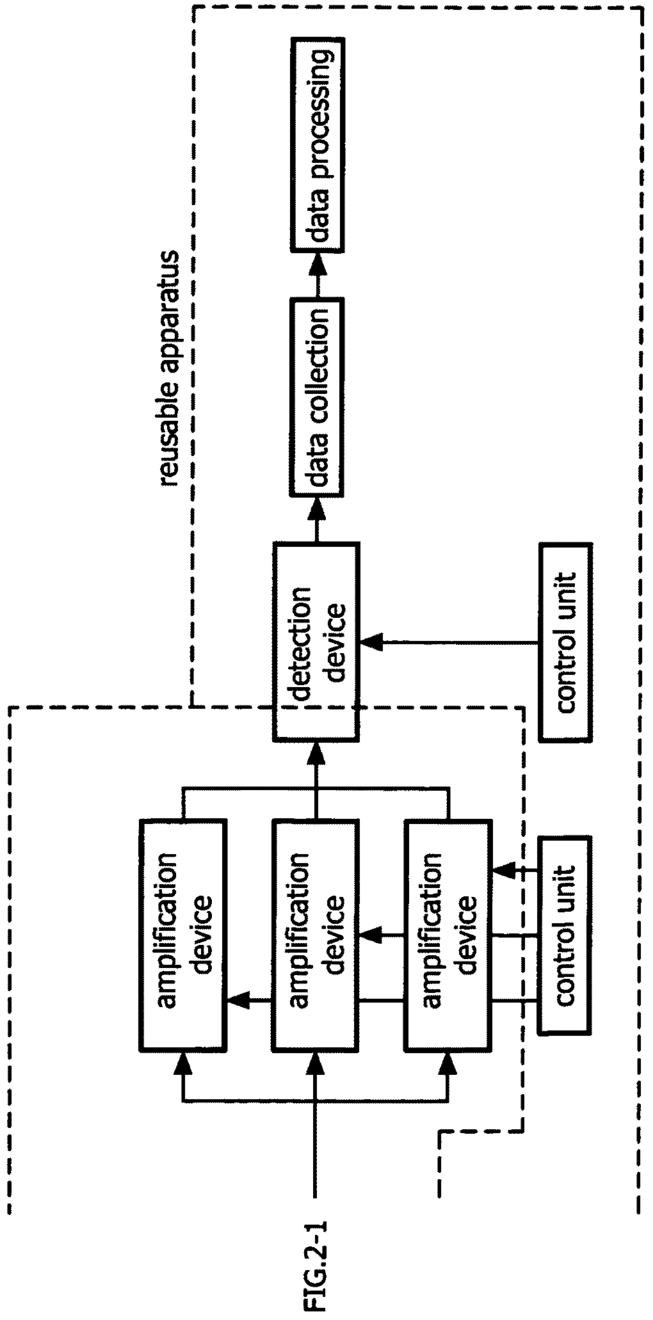

In FIG. 2 a schematic block diagram is shown in which the different process steps of the detection process using the method according the present invention are shown. This diagram is used to explain the main architecture of the cartridge 5 and the relation between the apparatus 2 and the cartridge 5.

In a first step ("sample insertion") a sample is introduced in the cartridge 5. For this purpose the cartridge 5 comprises an introduction device with which a sample can be introduced in the cartridge 5. The introduction device may for example be any suitable device for the introduction of a sample from a syringe or pipette or such, and may comprise a holding or docking device, a one-way inlet valve, a septum, filters, and an overflow. After introduction of the sample this sample may be guided to an introduction chamber.

In a second step ("lysis") the sample is treated to provide any nucleic acids in the sample in a form that they can be isolated from the sample. This lysis step typically includes the lysis of the cells such that cell and/or nuclear membranes are ruptured to thereby free the nucleic acids contained therein. The lysis step is carried out in a lysis chamber which is part of a lysis device. This lysis chamber is in fluid communication with the introduction device for the sample, for instance by means of a fluid channel. Pumping means may be provided for pumping the sample from the introduction chamber to the lysis chamber.

In a preferred embodiment the introduction chamber and lysis chamber are the same chamber.

In an embodiment the lysis device comprises a physical or mechanical manipulation means for the lysis step. In another embodiment, or the same embodiment, (also) chemical means can be used for lysis of the cells in the sample, such as a lysis buffer. Such lysis buffer may be held before use in a separate lysis buffer container which is in fluid communication with the lysis chamber. A valve, preferably a one-way valve, may be provided in the fluid channel connecting the lysis buffer container and the lysis chamber.

Means for mixing can be provided to mix the sample and the lysis buffer. These mixing means may be actuated by the apparatus.

The lysis and possibly the mixing is carried out under control of the control unit of the apparatus 2. The valves and pump means are actuated by the valve and pump means actuation devices being arranged in the apparatus 2.

Any waste fluid that is produced by the lysis step can be discarded, for instance to a waste device which may be present in the cartridge. Such waste device may be embodied as a waste chamber which is in fluid communication with the lysis chamber. In a third step ("enrichment"), an enrichment device, being arranged in the cartridge, enables the isolation of DNA from the lysed sample. To this end the enrichment device may be equipped with means for the isolation of DNA, such as magnetic particles.

The enrichment step is carried out in an enrichment chamber which is in fluid communication with the lysis chamber. In the fluid channel between lysis chamber and enrichment chamber a valve is provided to make it possible that only a flow through the fluid channel is possible when required. The valve may be actuable by the valve actuation means provided in the apparatus.

In this embodiment, the DNA or RNA of the present invention is absorbed onto magnetic particles. The absorbed nucleic acid material can be subjected to one or more washing, draining and/or purifying steps to remove any unwanted material such as remains of biological material contained in the sample and other sample components that are not DNA and/or RNA. This washing and purifying step is shown as a fourth step "washing and purifying" in FIG. 2. However, the "washing and purifying" step can also be regarded as a part of the "enrichment" step. When the absorbed DNA or RNA is of a desired purity, it can be desorbed or eluted from the magnetic particles. The washing and purifying step is carried out in a washing chamber. In the present embodiment this washing chamber is the same as the enrichment chamber. However, in other embodiments a separate chamber may be provided.

The cartridge 5 is provided with one or more washing buffer and elution buffer containers for holding the washing buffer(s) and elution buffer(s), respectively. Each of these washing buffer and elution buffer containers is in fluid communication with the washing chamber, and again each of the fluid channels providing this fluid communication is provided with a valve, preferably a one-way valve. Similar containers may be provided for any other reagents that are necessary for the enrichment step, i.e. the isolation of the DNA or RNA.

The valves of the enrichment device are actuated by the valve actuation device of the apparatus 2 and may be under control of the control unit 7.

In an alternative embodiment the enrichment device can also be equipped with physical or mechanical manipulation means of the fluids for mixing, separating and isolating the DNA or RNA. Such physical or mechanical manipulation means may be actuated by an actuation device of the apparatus 2 and may be under control of the control unit 7 of the apparatus.

Any waste produced from the enrichment step such as used buffers, washing fluids and the like can be guided to a waste device. This waste device which is part of the cartridge may be the same waste device as the waste device described in the lysis device. As an alternative, the waste devices of the lysis step and the enrichment step can be separate for each different purpose or volume.

In a fifth step ("pre-amplification") the total amount of DNA or RNA to be analysed may be increased by the use of a pre-amplification device. Subjecting DNA or RNA obtained from the isolation step to a pre-amplification step can increase the total amount of DNA. This is advantageously, especially in the case of multiplex analysis, where multiple tests are performed on the isolated DNA, for instance to detect the presence absence or amount of multiple pathogens in one sample at a time.

The pre-amplification device comprises a pre-amplification chamber in which the pre-amplification is carried out. The pre-amplification chamber may be the same chamber as or a different chamber than the enrichment chamber and/or washing chamber. The pre-amplification device is under the control of the control unit 7.

In the pre-amplification device, the isolated and purified DNA or RNA can be pre-treated with, inter alia an pre-amplification buffer and in case of whole genome amplification, with enzymes and DNTPs. Before use this pre-amplification buffer is held in a buffer container which is in fluid communication with the previous process chamber, for instance the washing chamber. A valve may in the fluid channel providing the fluid communication.

The pre-amplification device can be connected to a waste device for the disposal of materials.

In a sixth step ("amplification") the isolated DNA, optionally pre-treated as described herein elsewhere, is subjected in the amplification device to an amplification treatment. The amplification treatment comprises bringing the isolated DNA in contact with a set of PCR primers that are specific for the target nucleic acid, PCR enzymes such as one or more polymerases and dNTPs.

For this purpose the amplification device comprises a plurality of amplification chambers. The plurality of amplification chambers enables the isolated or pre-amplified DNA or RNA to be divided in portions and distributed amongst the chambers. In each chamber, an amplification step can be performed using a different set of primers. In this manner, multiplex analysis is provided in that one sample can be analysed for the presence, absence or amount of different target nucleic acids. In the case of multiplex analysis, the primer set for each target nucleic acid can be equipped with a detectably different label, i.e. with a different fluorescent spectrum.

The cartridge may comprise reagents containers for holding reagents for the amplification of the isolated DNA such as enzymes, DNTPs etc.

In a final step ("detection") the amplified DNA or RNA and preferably the labels that are incorporated in the amplification products are detected. For this purpose the system 1 comprises a detection device. This detection device comprises a detection chamber which is arranged on the cartridge 5. Other parts of the detection device may be arranged in the reusable apparatus 2 as described herein above. The detection chamber is in fluid communication with the one or more amplification chambers for simultaneously or subsequently introducing the DNA or RNA out of the one or more amplification chambers. Valves may be provided in the fluid channel connecting the detection chamber with the one or more amplification chambers.

The detection device can be under the control of the control unit 7. The detection device may detect based on label, length, mobility, nucleotide sequence, mass or a combination thereof. In certain embodiments a detection device can detect based on optical, electrochemical, magnetic or mobility (gel-electrophoresis). In principle any suitable detection device known from prior art may be used.

The detected information may be collected by data collection means and processed by data processing means to come for instance to a certain diagnose.

All fluid flows within the cartridge may be obtained by pump means which are provided in the cartridge. Such pump means may work on the basis of compressing or expanding spaces in the cartridge, in particular the spaces of the respective process chambers, i.e. the introduction chamber, the lysis chamber, the pre-amplification chamber, the washing and purifying chamber, the amplification chamber the and detection chamber, and the respective reagents containers. These pump means may also be of any other suitable type.

The pump means in the cartridge are actuated by the pump means actuation devices provided in the apparatus 2. These pump means actuation devices are under control of the control unit 7.

In the fluid paths or channels between the different process chambers i.e. the introduction chamber, the lysis chamber, the pre-amplification chamber, the washing and purifying chamber, the amplification chamber the and detection chamber, and the respective reagents containers, valves may be provided to only allow a flow when required. As most fluid will pass the fluid channels only in one direction the valves are preferably one-way valves.

The valves may be actuated by valve actuation devices which preferably are arranged in the apparatus 2.

All steps as described above may be under control of the control unit 7.

Figure 3:
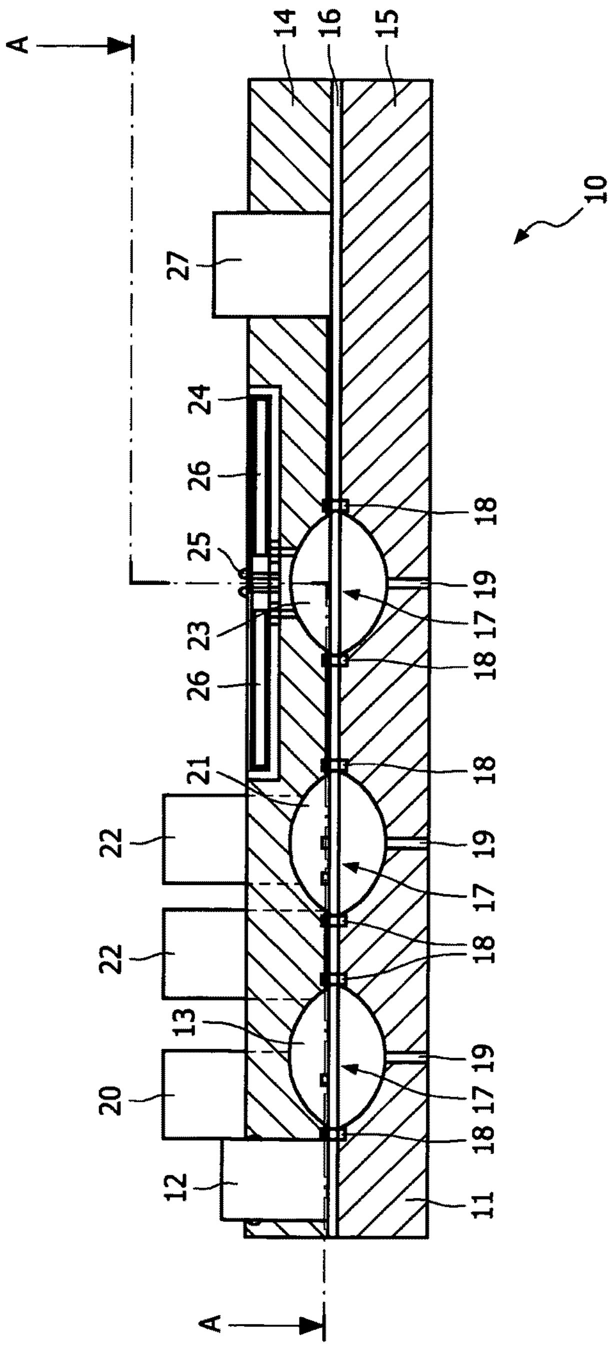
FIG. 3 shows a schematic cross section (B-B in FIG. 4) of an embodiment of a cartridge according to the present invention.
Figure 4:
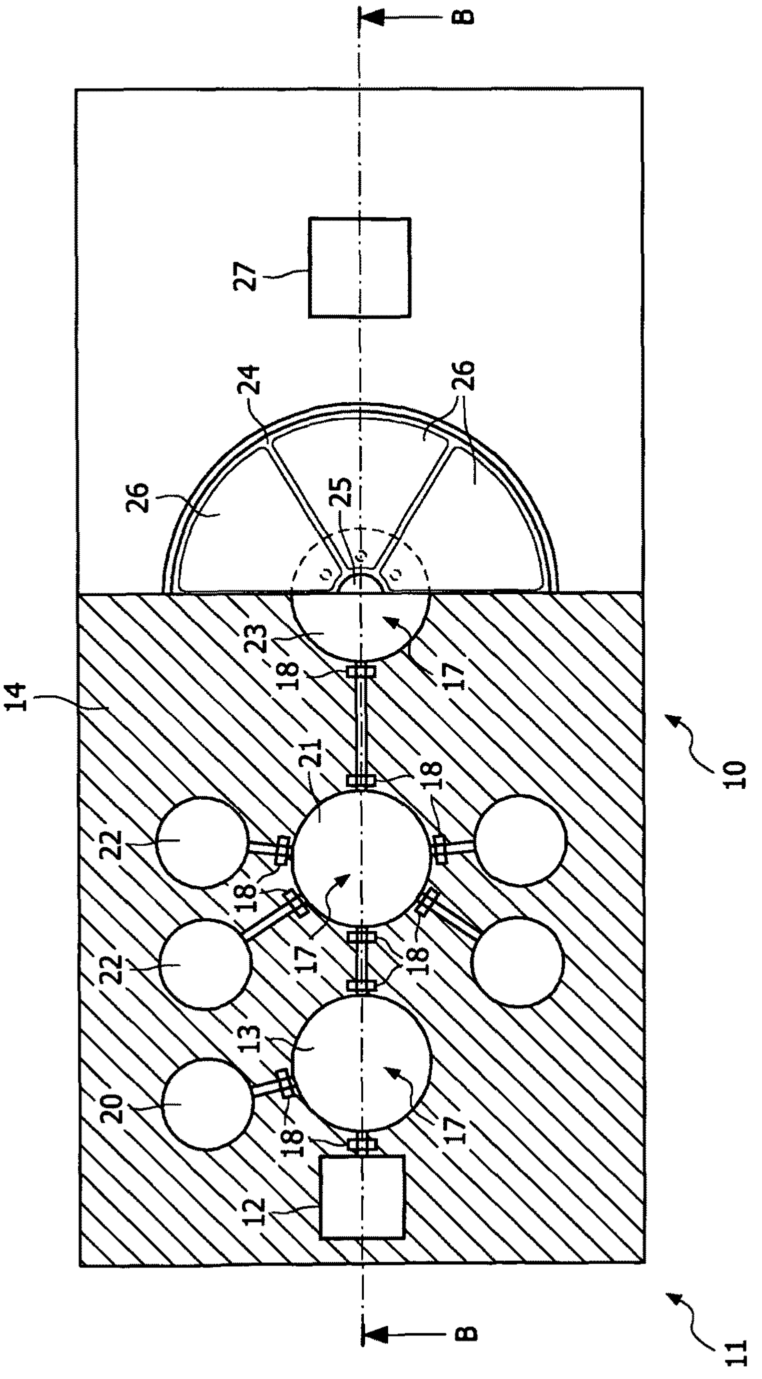
FIG. 4 shows a schematic top view/cross section (A-A in FIG. 3) of the embodiment of FIG. 3.

FIGS. 3 and 4 show in more detail an embodiment of a cartridge generally indicated with the reference numeral 10, in which the method as described above can be performed. The cartridge comprises a generic part 11 having a number of process chambers, and fluid handling systems as will be described hereinafter.

The different parts of the cartridge 10 will hereinafter be described in the order in which they will be used when a detection method for detection of the presence, absence and/or amount of a target nucleotide sequence in a sample comprising one or more nucleic acid sequences is performed.

The first application-specific part which is comprised in the cartridge 10 is a pre-lysis device 12. This pre-lysis device 12 is configured to process a sample to a certain state which can be processed by the cartridge 10.

For example the sample may be provided in a solid state, for instance dried out blood, while the cartridge is designed to process a sample in a fluid state. In such case the sample has to be brought into a fluid state before it can be processed in the cartridge. Such processing may be performed by providing suitable enzymes in a suitable medium in the pre-lysis device 12. Such processes are known in the art, such as for example trypsinization. By providing a pre-lysis device which can be connected to the generic part 11, the processing of the sample to the desired state can be performed without the need of transferring the sample after processing thereof therewith avoiding any chance on contamination. The processing of the sample to the desired state may be performed before or after that the pre-lysis device is connected to the generic part 11.

When no processing of the sample is needed, as the sample is already in a state which can be processed by the cartridge, the pre-lysis-device may also be indicated as a sample introduction device. The sample introduction device is then used to introduce the sample into the cartridge without risking any contamination, as the sample introduction device is designed to be connected to the generic part 11 for the introduction of the sample in the cartridge 10.

When the sample is introduced in the cartridge 10, it may be pumped to the lysis chamber 13. The generic part 11 of the cartridge 10 comprises fluid handling means including pumps and valves for pumping the sample to the different process chambers. In general the generic part 11 comprises two main components 14, 15 which are placed against each other with interposition of a flexible membrane 16. The two main components 14, 15 comprise recesses which together with the flexible membrane 16 may form pump chambers, valves, fluid channels, fluid storage stations and such.

In the cartridge shown in the drawings the sample will mainly be kept above the flexible membrane, while pumps 17 and valves 18 are mainly actuated from the bottom side of the flexible membrane 16. Fluid can be pumped in or out of a chamber by moving the flexible membrane to increase or decrease the space within the chamber, respectively. The flexible membrane can for example be moved by introducing air or fluid into the space between the flexible membrane 16 and the component 15. The air or fluid may be introduced through the channels 19. The other pump chambers may also be used as pump chambers in a corresponding way. Other means for moving the flexible membrane such as mechanical actuators may also be used. The valves may be actuated by air or fluid pressure, mechanical actuation or any other suitable actuation device. The movement of the flexible membrane 16 with respect to the component 14 may also be used to open and close a valve seat, whereby for example in the closed position of a valve the flexible membrane 16 is held against a channel end of the component 14.

In itself, such cartridge based systems having the type of pumps 17 and valves 18 for the handling of fluids as described, have been disclosed before, however, but not for the purpose of the present invention. Reference is made, inter alia, to U.S. Pat. No. 6,156,270, U.S. D37,164, U.S. D 351, 913, U.S. Pat. No. 6,382,923, U.S. Pat. No. 6,663,359, U.S. Pat. No. 6,416,293, U.S. Pat. No. 4,865,584 and U.S. Pat. No. 4,479,760.

In the lysis chamber 13 the sample will be lysed as hereabove described in step 2 in relation to FIG. 2. A lysis storage 20 is provided to store a lysis buffer before it is pumped in the lysis chamber.

After the lysis step the sample may be pumped to a second process chamber 21 wherein the sample may be enriched in accordance with step 3 and washed and purified in accordance with step 4 as described hereabove. Fluid storages 22 are provided for the storage of different washing and purifying buffers which may be used during the washing and purifying steps. These fluid storages 22 are in fluid communication via valves with the second process chamber 21.

After possible pre-amplification (as described in step 6 in relation to FIG. 2) which may also be performed in the second process chamber 21 or in the chamber 23, the sample may be introduced in the PCR body 24.

This PCR body 24 is a second application-specific part of the cartridge. The PCR body 24 is circular, disc shaped and connected with a click-fit connection 25 to the generic part 11.

The PCR body 24 comprises six thermocycling chambers 26 so that six PCR processes can be simultaneously be performed on the sample. Such PCR amplification process is hereabove described as step 6 in relation to FIG. 2. Each of the thermocycling chambers 26 is provided with at least one specific primer.

The PCR body 25 may be selected out of a group of different types of PCR bodies each comprising a different set of primers, a different number of chambers and/or a different chamber size or geometry. For instance the PCR body comprising the primers can be selected on the basis of the panels of bacteria/resistances that are to be detected, which selection may be specific for a particular assay or for a particular region, such as Europe, Asia or Africa.

The primers are spotted on a wall of the thermocycling chambers, for instance by an inkjet printing method, so that during storage of the PCR bodies no special measures have to be taken to avoid that the primers flow out of the PCR body, which would for instance be the case if primers in a fluid state would be used. In such case a seal or separate sealed chamber may be provided for holding the primers any other application-specific fluid before use thereof.

After the amplification step the amplified DNA or RNA and preferably the labels that are incorporated in the amplification products are pumped to the detection device 27. This detection device or at least a part thereof is a third application-specific part of the cartridge 10, which is a separate part and can be connected to the generic part 11. In the shown embodiment the detection device is connected to the generic part 11 by a click-fit connection.

Depending on the type of detection method and/or detection means (as described in this application; in particular step six described in relation to FIG. 2), a detection device may be chosen out a series of different application-specific detection devices which may be specially designed for each respective detection method.

In some cases the type of detection device that will be used in the cartridge 10 will be dependent on the type of PCR body which is used for the amplification process. Then the choice of a PCR body will automatically lead to a choice of the detection device.

The generic part 11 and the application-specific parts are provided with an identification device, so that after assembly of the generic and application-specific parts it can be checked whether the correct combination is made. Possibly, a more advanced identification system is used, as for instance a RF-tag, which comprises identification tags which automatically can be checked and of which possibly even the history can be tracked. Such checking and history tracking can be controlled by the control unit of the reusable apparatus as a step in the procedure for processing the sample in the cartridge.

An additional advantage of the construction of the present cartridge with a generic part and one or more application-specific parts is that the connection between the generic part and each of the application-specific parts can be easily made airtight, so that the entire space wherein the sample and other fluids used in the cartridge may be closed from the environment. In this way contamination of the sample during introduction of the sample in the cartridge and processing thereof is avoided and, since the sample is in a closed environment having its own internal pressure, the processing of the sample can be performed independent of the air pressure in the direct environment, and also independent of other environmental conditions as humidity. This makes a more reliable processing of the sample possible.

It is contemplated that the cartridge according to the present invention may comprise other application-specific parts than the application-specific parts identified in the above description. The application of such other separate application-specific parts in the cartridge are deemed to fall within the scope of the present invention. Examples of such application-specific parts may comprise fluid containers which contain a fluid such as enzymes, reagents, and other chemical substances for a specific application, mixing devices and other mechanical manipulation devices with different geometries or sizes for a specific application and others.

The invention may also be used for specific parts of the cartridge which have to be pre-treated or have to be kept at a certain temperature which is not desired or required for the other parts of the cartridge. For instance, the provision of a separate fluid container which can be used in the pre-treatment or stored at a different location, and which can consequently be connected to the generic part of the cartridge before use, may be very useful since the risk on contamination of that part, in particular the fluid therein is avoided, since the fluid does not have to be transferred from a container to the cartridge in an open environment.

Such use of a separate part is regarded to be application-specific within the meaning of the present invention, even if the same part is used in a number of different applications. An example of such separate part is a separate fluid container for a so-called PCR master mix which has to be stored at a low temperature before use on the cartridge. Just before the cartridge is introduced into the reusable apparatus, the separate fluid container is connected to the generic part of the cartridge, for example by a click fit connection.

FIGS. 5 and 6 describe in more detail a generally disk shaped PCR body as a whole indicated with the reference numeral 30. The PCR body 30 comprises six thermocycling chambers 31, each being capable of holding a fluid during a PCR process. The PCR body 30 comprises a ring shaped main part 32 and six fingerlike flexible parts 33. Fingerlike in this context means that the flexible parts 33 are connected at one end, in this case the radially outer ends, with the ring shaped main part 32, while the opposite end is free, i.e. not fixedly connected to any part of the PCR body 30. In other words, the flexible parts 33 are only at one side connected with the ring shaped main part 32, while the other sides are free. Due to this fingerlike construction the flexible parts 33 are flexible in the direction perpendicular to the main plane of the disk shaped PCR body 30 (in FIG. 6 in upwards or downwards direction).

At the bottom side of the thermocycling chambers 31 a fluid opening 34 is provided in order to make fluid exchange between a thermocycling chambers 31 and a process chamber in another part of the cartridge possible. This fluid opening 34 is located at the end of the flexible part 33 which is remote of the ring shaped main part 32, so that this fluid opening 34 and an associated sealing surface 35 may be biased in the direction of the main part of the cartridge with which the PCR body 30 is connected. This biasing of the flexible parts 33 is obtained by biasing means. These biasing means may be comprised in the PCR body 30 and/or in the main part of the cartridge. In the present embodiment, the biasing means are comprised in a separate locking device, which is also used to lock the PCR body 30 of the main part of the cartridge. This locking device will further be described in relation to FIG. 7.

By biasing the flexible parts 33, or at least the location of the fluid opening 34 and associated sealing surface 35, a better sealing between the PCR body 30 and the main part of the cartridge is obtained. Such proper sealing is of importance, since in this way leakage of the fluid contained in the cartridge, and more importantly contamination of this fluid is avoided. Furthermore, since the cartridge is preferably a closed system, as was described hereinabove, the biasing of the PCR body towards the main part of the cartridge prevents leakage and contamination in particular when the pressure inside in the fluid system of the cartridge is higher than the outside environmental (air) pressure. In the embodiment as shown in FIGS. 5 and 6 the sealing surfaces 35 lie substantially parallel to each other, which has the advantage that biasing the whole PCR body towards the main part improves the sealing of all fluid openings 34 with respect to the main part. The sealing is further improved by the several flexible parts 33 which were described above.

Now, the construction of the PCR body 30 will be described in more detail. The PCR body 30 comprises a component 36 comprising the ring shaped main part 32 and the six flexible parts 33. In each of the six flexible parts 33 a recess is provided, which recess delimits the bottom and the sides of the thermocycling chambers 31. On top of the component 36 a foil 37 is arranged to the limit the upper side of the thermocycling chambers 31. The foil 37 may be flexible, in such a way that when fluid is pumped into the thermocycling chambers, the foil 37 is stretched so that the space within the thermocycling chambers 31 is increased. The elasticity of the foil 37 may then be used to pump the fluid back out of the thermocycling chambers 31. In the case a flexible foil 37 is designed to stretch out due to the pressure provided in the thermocycling chambers 31, the recess provided in the component 36 may be substantially smaller than shown in the embodiment of FIG. 7, or may even be omitted.

The foil 37 may be connected with the component 36 with any known measure, such as using a glue, (double-sided) tape, welding and melting. Instead of foil also a more rigid material may be used to close the recesses to form the thermocycling chambers 31. However, foil may be preferred in view of the above mentioned stretching capabilities and the low weight. Further, the foil or other material may be made transparent so that the inside of the thermocycling chambers 31 can be seen, and/or be given a specific color which can be used as a code to indicate the type of PCR body, for instance in the specific set of primers.

The component 36 is preferably made of a plastics in an injection mold process. However, the component 36 may also be made of any other suitable material, and by any suitable process. The foil 37 is also preferably made of plastics material.

The PCR body 30 further comprises a seal element 38 which comprises the sealing surface 35, and a part of the fluid opening 34. The seal element 38 is preferably made of a relatively soft material which is suitable as a seal material, such as for instance a rubber. By providing a separate seal element 38 the sealing between the PCR body 30 and the main part of the cartridge can be improved as the material and shape of the seal element 38 can be in particular designed for the sealing.

After connection of the PCR body 30 on the main part of the cartridge, the PCR body 30 can be rotated with respect to the main part of the cartridge between a first open position in which the fluid opening 34 is in fluid communication with a fluid opening on the main part of the cartridge, and a second closed position in which the fluid communication between the fluid opening 34 and the associated fluid opening on the main part of the cartridge is closed. It will be clear for the man skilled in the art that in both the open and the closed position the sealing between the PCR body 30 and the main part of the cartridge has to be sufficient in order to prevent leakage and contamination. Therefore, for both the open and closed position the seal element 38 as been provided with proper sealing surface is 35 for the open position (left side of FIG. 6) and the closed position (right side of FIG. 6). In FIG. 7 the seal element 38 is shown in more detail.

By moving the PCR body 30 with respect to the main part of the cartridge between the open and closed positions, the transition between those two parts is used as a valve. This is advantageous since no separate valve mechanism is needed in order to open and/or close the fluid communication between the thermocycling chambers 31 and the main part of the cartridge. This is in particular advantageous in the application of the present invention, since relatively small quantities of fluid are used. The presence of a separate valve mechanism would require extra space for fluid which extra space will have to be filled with fluid after fluid has been pumped through the valve mechanism. This fluid can then not anymore be used in the PCR process.

In the embodiment shown in FIGS. 5 and 6, all fluid openings 34 are brought in fluid communication with the fluid openings of the main part of the cartridge in the open position, while for all fluid openings 34 the fluid communication is closed in the closed position. In an alternative embodiment it is possible that the open position for some fluid openings 34 corresponds with the closed position for other fluid openings 34, i.e. that some fluid openings 34 are in fluid communication with the main part, while other fluid openings 34 are closed. Also, it is possible to provide more open and/or closed positions, so that selectively one or more fluid openings 34 can be brought in fluid communication with the main part, while others are closed. For instance, with a PCR body with six thermocycling chambers, there may be a first open position in which three fluid openings are in fluid communication with the main part while the other three fluid openings are closed, a second open position in which the other three fluid openings are in fluid communication with the main part and the first three fluid openings are closed, and a closed position wherein all fluid openings are closed. The same PCR body may also comprise seven positions, comprising for instance a closed position in which all fluid openings are closed, and six open positions in which a selective one of the fluid openings is in fluid communication with the main part, while the other fluid openings are closed. In the present embodiment it is preferred to open all fluid openings 34 simultaneously so that during one pumping action all thermocycling chambers can be filled with the same amount of fluid.

In the exterior circumference of the ring shaped main part 32 of the PCR body 30, a recess 39 is provided so that the rotational position of the PCR body 30 with respect to the main part of the cartridge is known. For this reason a notch is provided in the cartridge which can be placed in the recess 39. The recess 39 can also be used to rotate the PCR body 30 between the open and closed positions. However, in the present embodiment this rotation is transferred to the PCR body 30 by the locking device (which shown in FIG. 8).

In the present embodiment, the PCR body 30 comprises six thermocycling chambers 31 on six a different flexible parts 33. Depending on the actual application for which the PCR body 30 is used, a different number of thermocycling chambers 31 with the same or a different volume may be provided. One or more of these thermocycling chambers 31 may be provided on one flexible part 33. In such embodiment it is also possible that one thermocycling chamber 31 comprises two or more fluid openings 34 or that one fluid opening 34 is connected with two or more thermocycling chambers 31. With such embodiments of the PCR body 30, one generic main part of the cartridge having a certain number of fluid openings to connect with the PCR body, can easily be used for PCR bodies having a different number of thermocycling chambers.

FIG. 8 shows a perspective view of a PCR body 40 with ten thermocycling chambers each provided on a flexible part 43, connected to the main part 41 of the cartridge. For locking the PCR body 40 on the main part 41 of the cartridge, a locking device 42 is provided, which is placed through the center of the disk shaped PCR body 40. The locking device 42 has a click-fit connection with the main part 41 of the cartridge, but any other suitable connection means such as screw or snap-on means may be used. The locking device 42 comprises a number of biasing means in the form of spring elements 44 which each bias one of the flexible parts 43 of the PCR body towards the main part 41. Furthermore, the locking device 42 as shown in FIG. 8 is designed to fix the rotational position of the PCR body 40, since the PCR body can only be placed in one position with respect to the locking device 42.

As the flexible parts 43 are flexible in the direction in which they are biased, the spring elements 44 push the sealing surfaces of the PCR body against the associated sealing surfaces of the main part 41. This provides a proper sealing between the main part 41 and the PCR body 40 and therewith prevents leakage of fluid and/or contamination of the system.

The top end 45 of the locking device 42 is designed to be connected with an actuator in the reusable apparatus for actuation of the rotational movement of the PCR body 40 between the open and the closed position.

It will be clear for the man skilled in the art that the connection according to the invention between the PCR body 40 and the main part 41 of the cartridge as described herein above may also be applied to any other combination of two components which is used in the cartridge, and between which fluid is exchanged during the detection process. All such embodiments are into fall within the scope of the present invention.

The invention claimed is:

1. A cartridge for the detection of the presence, absence and/or amount of a target nucleotide sequence in a sample comprising one or more nucleic acid sequences, the cartridge comprising:

a first component for processing a fluid having a sample, said first component including:
one or more processing chambers,
a first fluid opening for fluid access to at least one of said processing chambers of the first component, and
a first sealing surface associated with the first fluid opening;
a second component connectable to the first component for processing the fluid, said second component including:
one or more processing chambers,
a second fluid opening for fluid access to at least one of said processing chambers of the second component, said second fluid opening formed in a flexible portion of the second component that is at least flexible in a direction perpendicular to the second sealing surface, and
a second sealing surface associated with the second fluid opening,
the first and second components are moveable relative to each other when the first component is connected to the second component to selectively position the first and second fluid openings in (i) an open fluid communication position, wherein the first fluid opening is generally aligned with the second fluid opening to allow the fluid to move between the first component and the second component, and (ii) a closed fluid communication position, wherein the first fluid opening is unaligned with the second fluid opening to prevent the fluid from moving between the first component and the second component; and
a biaser for biasing the second sealing surface toward the first sealing surface to engage the second sealing surface with the first sealing surface to provide a sealed fluid pathway between the first and second components, thereby preventing fluid from leaking external to said cartridge.

2. A cartridge according to claim 1, wherein the second component comprises two or more flexible portions, each having a second fluid opening and an associated second sealing surface and each being at least flexible in a direction perpendicular to the respective second sealing surface.

3. A cartridge according to claim 1, wherein the first and second sealing surfaces are substantially flat, the planes of each of the first and second sealing surfaces being substantially parallel to each other.

4. A cartridge according to claim 1, wherein the second component is disk shaped and comprises a ring-shaped main body and a plurality of fingerlike flexible parts, one end of each flexible part being connected to the main body and an opposite end of the flexible part being free, wherein the second fluid opening and the second sealing surface are provided at the opposite end of the flexible part.

5. A cartridge according to claim 1, wherein the first component is a main part of the cartridge, and the second component is a PCR body comprising said one or more processing chambers.

6. A cartridge according to claim 5, wherein said second fluid opening is an inlet and outlet for one of the one or more processing chambers of the second component.

7. A cartridge according to claim 4 wherein each of the one or more processing chambers of the second component are formed by a space between the main body and a flexible foil joined to the main body at the edges of the space, the second fluid opening being in fluid communication with the space.

8. A cartridge according to claim 1, wherein the biaser is comprised of a locking device to lock the second component to the first component.

9. A cartridge according to claim 8, wherein the locking device comprises at least one spring element to bias the second sealing surface in the direction of the first sealing surface.

10. A cartridge according to claim 9, wherein after connection of the first component to the second component, the first and second components are rotatable relative to each other around an axis of rotation, and wherein the first and second component each comprise two or more fluid openings being substantially arranged in a circle around the axis of rotation.

11. A cartridge according to claim 1, wherein at least one of the first or second sealing surfaces is made of a relative soft material.

12. A cartridge according to claim 1, wherein at least one of the first and second components is provided with a seal element comprising the first fluid opening and first sealing surface or the second fluid opening and second sealing surface, respectively, the seal element being configured as a valve to provide in the open fluid communication position a fluid communication between the first and second fluid openings, and to provide in the closed fluid communication position an obstruction of the fluid communication, the seal element further being configured to seal the first and second fluid openings from the environment in both the open and closed fluid communication positions.

13. A cartridge according to claim 8, wherein the locking device is configured to be used to move the second component between a first and second position.

14. A cartridge for the detection of the presence, absence and/or amount of a target nucleotide sequence in a sample comprising one or more nucleic acid sequences, the cartridge comprising:

a first component for processing a fluid having a sample, said first component including:

one or more processing chambers, a first fluid opening for fluid access to at least one of said processing chambers of the first component, and a first sealing surface associated with the first fluid opening;

a second component connectable to the first component for processing the fluid, said second component including:

a disk shaped body including at least one flexible portion, one or more processing chambers located within the disk shaped body, a second fluid opening formed in the at least one flexible portion, the second fluid opening providing fluid access to at least one of said processing chambers of the second component, and a second sealing surface associated with the second fluid opening, the first and second components moveable relative to each other when the first component is connected to the second component, for selectively positioning the first and second fluid openings in (i) an open fluid communication position, wherein the first fluid opening is generally aligned with the second fluid opening to allow the fluid to move between the first component and the second component, and (ii) a closed fluid communication position, wherein the first fluid opening is unaligned with the second fluid opening to prevent the fluid from moving between the first component and the second component; and a biaser for biasing the second sealing surface toward the first sealing surface to engage the second sealing surface with the first sealing surface, wherein engagement of said first sealing surface with said second sealing surface provides a sealed fluid pathway between the first and second components, thereby preventing the fluid from leaking external to said cartridge.

15. The cartridge according to claim 14, wherein upon connection of the first component to the second component, the first and second components are rotatable relative to each other.

16. The cartridge according to claim 14, wherein being positioned to provide fluid communication between the first and second fluid openings, the second sealing surface is structured and arranged to be positionable in relation to the first sealing surface to close the fluid communication.

17. The cartridge according to claim 14, further comprising a locking device postionable to lock the second component to the first component, the locking device comprising the biaser.

18. The cartridge according to claim 17, wherein the biaser comprises at least one spring element to bias the second sealing surface in the direction of the first sealing surface.

* * * * *